(12) United States Patent
Altmann et al.

(10) Patent No.: US 11,819,331 B2
(45) Date of Patent: Nov. 21, 2023

(54) VISUALIZATION OF EPICARDIAL AND ENDOCARDIAL ELECTROANATOMICAL MAPS

(71) Applicant: BIOSENSE WEBSTER (ISRAEL) LTD., Yokneam (IL)

(72) Inventors: Andres Claudio Altmann, Haifa (IL); Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 0 days.

(21) Appl. No.: 17/545,387

(22) Filed: Dec. 8, 2021

(65) Prior Publication Data
US 2023/0172516 A1    Jun. 8, 2023

(51) Int. Cl.
*G06T 11/00* (2006.01)
*A61B 5/339* (2021.01)
*A61B 5/367* (2021.01)

(52) U.S. Cl.
CPC .............. *A61B 5/339* (2021.01); *A61B 5/367* (2021.01); *G06T 11/00* (2013.01)

(58) Field of Classification Search
None
See application file for complete search history.

(56) References Cited

U.S. PATENT DOCUMENTS

| | | | |
|---|---|---|---|
| 6,895,267 B2 | 5/2005 | Panescu | |
| 8,456,182 B2 | 6/2013 | Bar-Tal | |
| 10,039,464 B2 * | 8/2018 | Dubois | G06F 30/23 |
| 2007/0003119 A1 * | 1/2007 | Roehrig | G16H 10/60 |
| | | | 382/128 |
| 2014/0200467 A1 * | 7/2014 | Strom | A61B 5/0044 |
| | | | 600/300 |
| 2014/0200473 A1 | 7/2014 | Zeng | |
| 2015/0164357 A1 * | 6/2015 | Zeng | A61B 5/7278 |
| | | | 607/18 |
| 2015/0216438 A1 * | 8/2015 | Bokan | A61B 5/316 |
| | | | 600/515 |
| 2017/0337211 A1 * | 11/2017 | Netsch | G16H 10/20 |
| 2017/0360319 A1 * | 12/2017 | Hagfors | A61B 5/743 |
| 2018/0078312 A1 * | 3/2018 | Trayanova | G06T 7/11 |
| 2018/0199847 A1 | 7/2018 | Markovitz | |

(Continued)

FOREIGN PATENT DOCUMENTS

| | | |
|---|---|---|
| EP | 1897490 A2 | 3/2008 |
| JP | H1032335 A | 12/1998 |

OTHER PUBLICATIONS

Wang, Linwei, et al. "Non-invasive epicardial and endocardial electrocardiogramaging for scar-related ventricular tachycardia." Ep Europace 20.FI2 (2018): f263-f272. (Year: 2018).*

(Continued)

*Primary Examiner* — Yu Chen

(57) ABSTRACT

A method includes receiving a first representation of an internal surface of at least a portion of a wall of an organ of a patient, and a second representation of an external surface of at least the portion of the wall of the organ. The first and second representations are registered with one another. An exploded representation is generated from the first and second representations, that shows both the internal surface and the external surface. The exploded representation is presented to a user.

14 Claims, 3 Drawing Sheets

(56) References Cited

U.S. PATENT DOCUMENTS

| | | | |
|---|---|---|---|
| 2018/0206921 A1* | 7/2018 | Pappone | A61B 18/12 |
| 2019/0000562 A1* | 1/2019 | Thienphrapa | A61B 34/20 |
| 2019/0304186 A1* | 10/2019 | Wang | G16H 30/40 |
| 2020/0085329 A1* | 3/2020 | Markovitz | A61B 5/287 |
| 2020/0214662 A1* | 7/2020 | Konofagou | A61B 5/339 |
| 2020/0326839 A1* | 10/2020 | Walkin | G06F 3/04845 |
| 2023/0036977 A1* | 2/2023 | Zeng | A61B 5/327 |

OTHER PUBLICATIONS

Tung, Roderick, et al., "Simultaneous Endocaridal and Epicardial Delineation of 3D Reentrant Ventricular Tachycardia", Journal of the American College of Cardiology, vol. 75, No. 8, Feb. 24, 2020 pp. 884-897.

Zhang, Yongjie et al., "an atlas-based geometry pipeline for cardiac hermite model construction an diffusion tensor reorientation", Medical Image Analysis, vol. 16, No. 6, Aug. 1, 2012.

* cited by examiner

VISUALIZATION OF EPICARDIAL AND ENDOCARDIAL ELECTROANATOMICAL MAPS

FIELD OF THE DISCLOSURE

The present disclosure relates generally to cardiac mapping, and particularly to visualizing anatomical cardiac maps.

BACKGROUND OF THE DISCLOSURE

Various graphical tools for assisting the analysis of a rendering of an organ were proposed in the literature. For example, Tung et al. describe high-resolution simultaneous endocardial and epicardial mapping, in a paper titled, "Simultaneous Endocardial and Epicardial Delineation of 3D Reentrant Ventricular Tachycardia," Journal of the American College of Cardiology Volume 75, Issue 8, Mar. 3, 2020, Pages 884-897. The authors use therein a 3D perspective view of the endocardial and epicardial surfaces.

As another example, U.S. Patent Application Publication No. 2007/0003119 describes display and navigation methods for multiple computer-aided detection (CAD) detections. A medical image is displayed to a viewer, and a request is received to instantiate CAD-assisted viewing. A timewise presentation sequence for the CAD detections is automatically computed according to a predetermined sequencing criterion. For each CAD detection, an expanded presentation 2-dimensional window floating on a computer screen is displayed for its associated location in the medical image, the expanded presentation windows being displayed according to the timewise presentation sequence.

BRIEF DESCRIPTION OF THE DRAWINGS

The present disclosure will be more fully understood from the following detailed description of the examples thereof, taken together with the drawings in which.

DETAILED DESCRIPTION OF EXAMPLES

Overview

Figure 1:
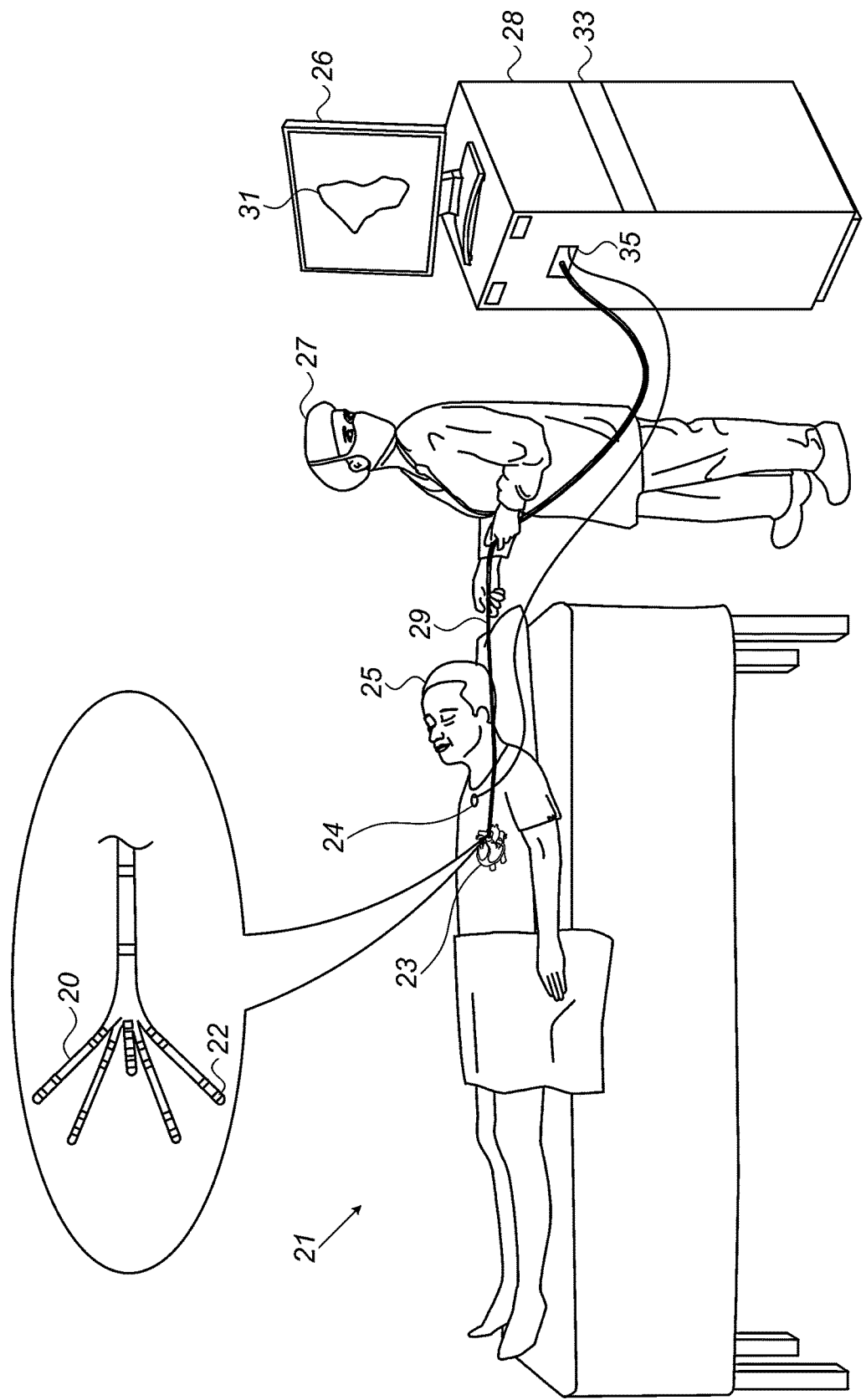
FIG. 1 is a schematic, pictorial illustration of a system for electroanatomical (EA) mapping, in accordance with an example of the present disclosure.

Catheter-based electroanatomical (EA) mapping techniques may produce various EA maps of an organ, such as a left atrium of a heart. In some cases, to interpret the EA maps, a physician needs to compare two different EA maps. For example, during or after a cardiac EA mapping of a cardiac chamber, a physician may want to view EA maps of both the epicardial and endocardial surfaces of the cardiac chamber. However, the analysis task is difficult because, when both EA maps are presented to the physician overlaid on one another, one map obscures the other.

Some examples of the present disclosure that are described hereinafter provide a processor that receives a first representation of an internal surface of at least a portion of a wall of an organ of a patient, and a second representation of an external surface of at least the portion of the wall of the organ. The processor registers each representation with the other and generates an exploded representation to show both surfaces.

To this end, the processor generates first and second clipped views of the first and second representations, respectively, and displaces the clipped views along a predefined direction. The displacement causes the first and second clipped views to not overlap one another.

In some examples, the received first and second representations are EA maps of epicardial and endocardial surfaces, respectively, of a same portion of a cardiac chamber. In an example, a processor generates one surface 3D reconstruction (usually representing the endocardial anatomy). The epicardial surface is colored according to the epicardial electrical information projected from the mapping catheter position at the endocardial surface. The internal side of the map is colored according to the endocardial electrical signals. The displaced clipping views for visualization prevents either EA map being obscured at a selected portion.

In another example, the processor uses a colored scale, with a draggable threshold value, to differentiate between endocardial and epicardial electrical properties in a same region.

In another example, the processor visualizes the endocardial and the respective epicardial surfaces by placing a virtual camera internally to the map to display the endocardial information.

In an implementation, the processor uses only the outer surface and displays epicardial information in one texture and the endocardial in another texture. In this way, the correlated activation and the non-correlated activation is immediately visualized.

Typically, the processor is programmed in software containing a particular algorithm that enables the processor to conduct each of the processor-related steps and functions outlined above.

The disclosed techniques may assist the physician in the interpretation of epicardial and endocardial EA maps. The disclosed technique may thus expedite and improve the quality of complicated diagnostic tasks, such as those required in diagnostic catheterizations.

System Description

FIG. 1 is a schematic, pictorial illustration of a system 21 for electroanatomical (EA) mapping, in accordance with an example of the present disclosure. FIG. 1 depicts a physician 27 using an EA Pentaray® catheter 29 to perform an EA mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject unipolar and/or bipolar signals from and/or to the tissue of heart 23. A processor 28 receives these signals via an electrical interface 35, and uses information contained in these signals to construct an exploded representation 31, such as exploded EA map 31 comprising EP values (e.g., LAT values), a color-coded endocardium, and epicardium surfaces that processor 28 stores in a memory 33. During and/or following the procedure, processor 28 may display EA map 31 on a display 26.

Figure 2:
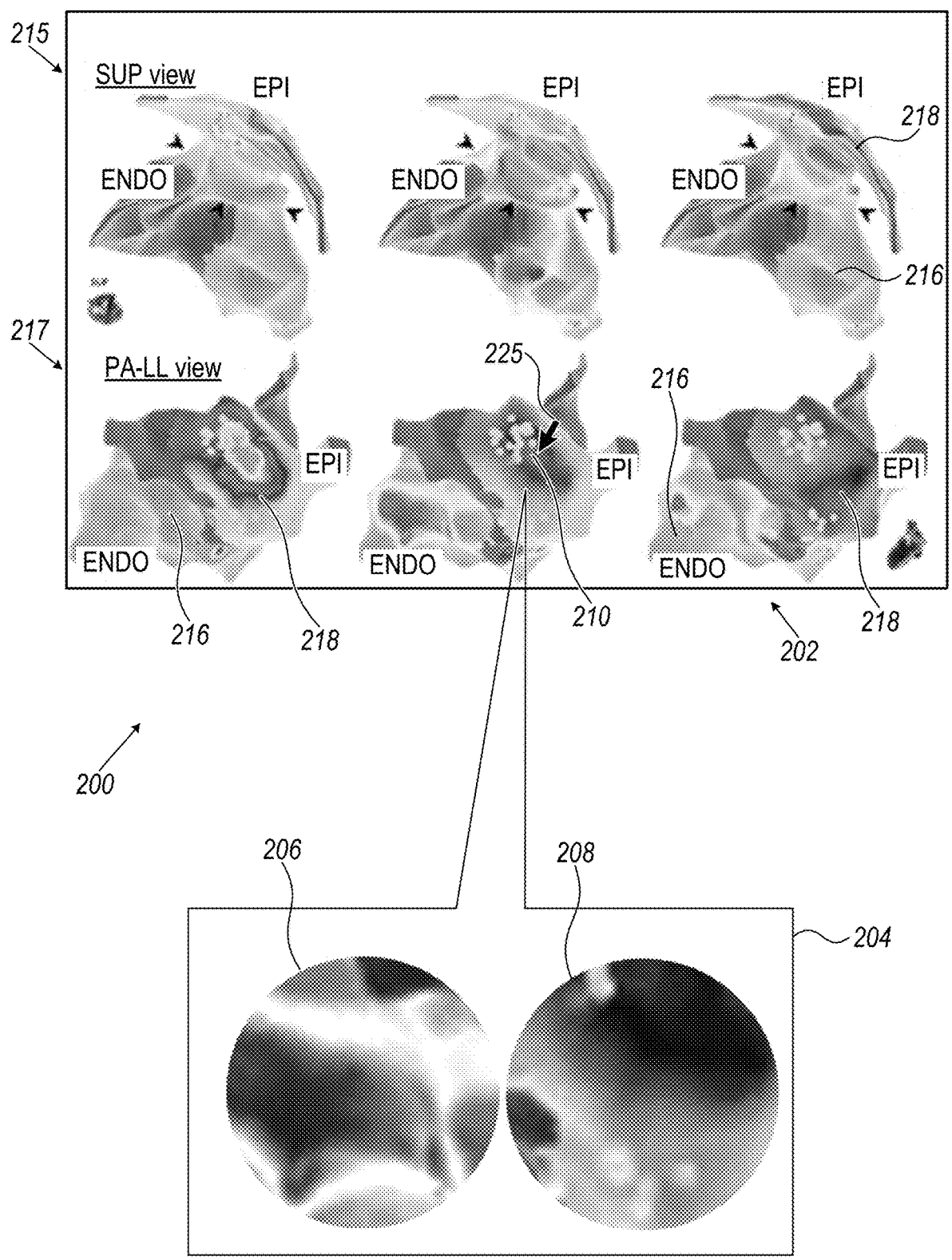
FIG. 2 shows schematic, pictorial volume renderings of exploded electroanatomical (EA) maps of endocardial and epicardial surfaces displayed on a graphical user interface (GUI), in accordance with an example of the present disclosure.

In some examples, exploded EA map 31 comprises a draggable circular overlay region, in order to display a side-by-side view of endocardium and epicardium surfaces of a same region of exploded EA map 31, as shown in FIG. 2.

During the procedure, a tracking system is used to track the respective locations of sensing-electrodes 22, such that each of the signals may be associated with the location at which the signal was acquired. For example, the Active Current Location (ACL) system, made by Biosense-Webster (Irvine California), which is described in U.S. Pat. No. 8,456,182, whose disclosure is incorporated herein by reference, may be used. In the ACL system, a processor estimates the respective locations of the electrodes based on impedances measured between each of the sensing-electrodes 22, and a plurality of surface-electrodes 24, that are coupled to the skin of patient 25. For example, three surface-electrodes 24 may be coupled to the patient's chest, and another three surface electrodes may be coupled to the patient's back. For ease of illustration, only one surface-electrode is shown in FIG. 1. Electric currents are passed between electrodes 22 inside heart 23 of the patient, and surface electrodes 24. Processor 28 calculates an estimated location of all electrodes 22 within the patient's heart based on the ratios between the resulting current amplitudes measured at surface electrodes 24 (or between the impedances implied by these amplitudes) and the known positions of electrodes 24 on the patient's body. The processor may thus associate any given impedance signal received from electrodes 22 with the location at which the signal was acquired.

The example illustration shown in FIG. 1 is chosen purely for the sake of conceptual clarity. Other tracking methods can be used, such as ones based on measuring voltage signals. Other types of sensing catheters, such as the Lasso® Catheter (produced by Biosense Webster) may equivalently be employed. Contact sensors may be fitted at the distal end of EA catheter 29. As noted above, other types of electrodes, such as those used for ablation, may be utilized in a similar way, fitted to electrodes 22 for acquiring the needed position data. Thus, an ablation electrode used for collecting position data is regarded, in this case, as a sensing electrode. In an optional example, processor 28 is further configured to indicate the quality of physical contact between each of the electrodes 22 and an inner surface of the cardiac chamber during measurement.

Processor 28 typically comprises a general-purpose computer with software programmed to carry out the functions described herein. In particular, processor 28 runs a dedicated algorithm as disclosed herein, including in FIG. 3, that enables processor 28 to perform the disclosed steps, as further described below. The software may be downloaded to the computer in electronic form, over a network, for example, or it may, alternatively or additionally, be provided and/or stored on non-transitory tangible media, such as magnetic, optical, or electronic memory.

Epicardial and Endocardial View on One 3D Electroanatomical Map

FIG. 2 shows schematic, pictorial volume renderings of exploded electroanatomical (EA) maps 202 of endocardial and epicardial surfaces displayed on a graphical user interface (GUI) 200, in accordance with an example of the present disclosure.

As seen, the processor has generated rendered clipped views of the endocardial and epicardial surfaces 216 and 218. Furthermore, the processor having displaced each of the clipped views along one predefined direction 215, and along a second predefined direction 217. Direction 215 is named in FIG. 2 "SUP view" and direction 217 is named therein "PA-LL view."

In another example, the processor receives first and second representations 216 and 218, in the form of the endocardial and epicardial surfaces 216 and 218, respectively.

As further seen, FIG. 2 shows a draggable circular overlay 210. A separate window 204 shows a side-by-side corresponding circular region color-coded EA map 206 of the endocardium surface and circular region color-coded EA map section 208 of the epicardium surface, for a same region defined by circular overlay 210. The physician may move circular overlay 210, for example, using a marker 225 to drag the circle, and also change the radius of circular overlay 210. Using overlay 210, the physician can, for example, quickly check whether or not a cardiac tissue region is entirely inactive without switching (i.e., toggling) between the two EA maps.

While FIG. 2 shows a circular overlay, the overly may have another shape, such as, for example, one that provides an isometric view that varies with location over the cardiac chamber. Furthermore, the disclosed technique may be used to create a multi-view map that comprises three or more overlay regions, with additional information shown on top of the endocardial and epicardial surface information, such as an overlay indicating, for example, cardiac wall thickness at the region.

Figure 3:
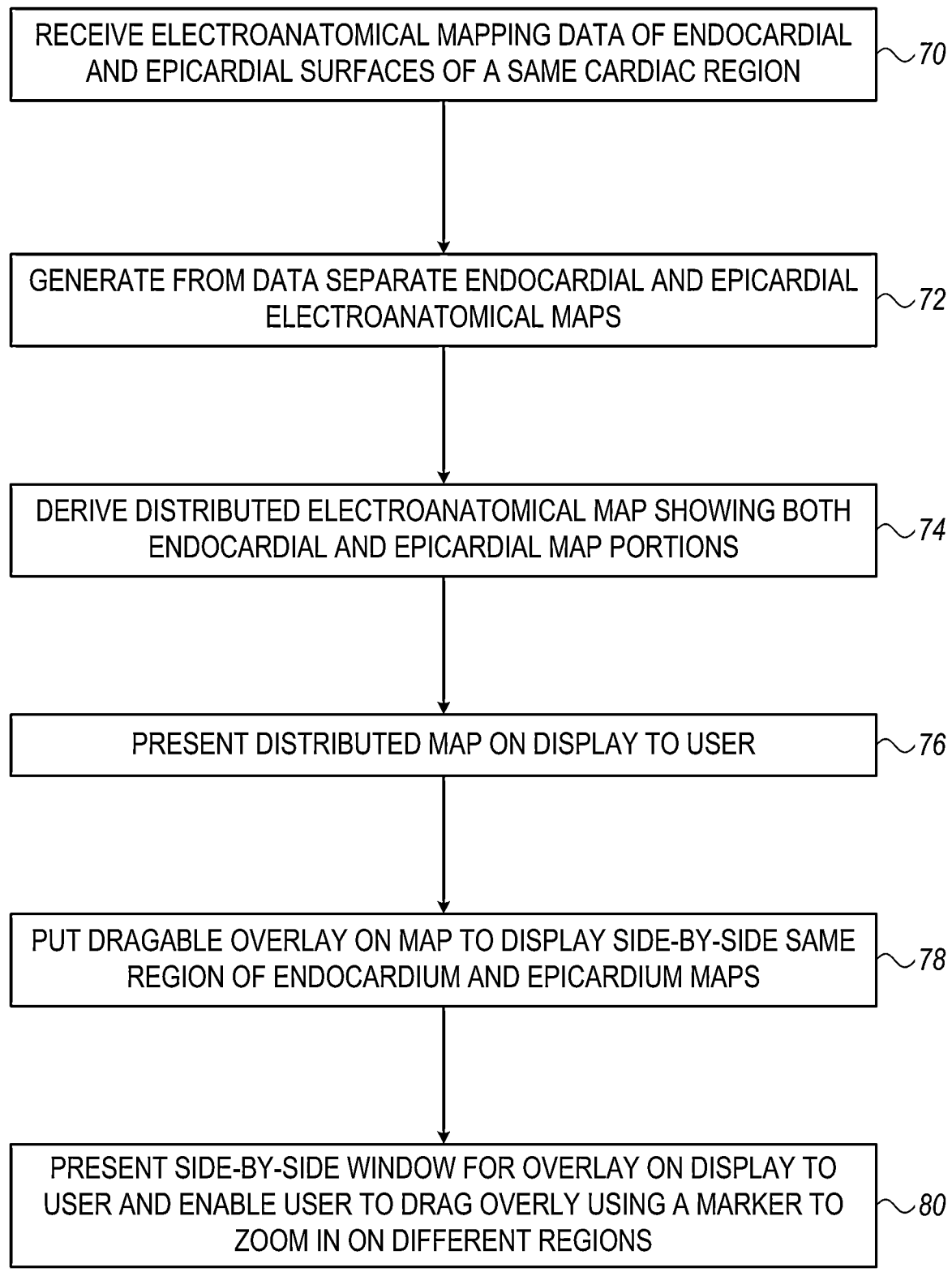
FIG. 3 is a flow chart that schematically illustrates a method for generating the exploded EA maps of FIG. 2 and a related side-by side view, in accordance with an example of the present disclosure.

FIG. 3 is a flow chart that schematically illustrates a method for generating the exploded EA maps 202 and related side-by-side viewing window 204 of FIG. 2, in accordance with an example of the present disclosure.

The algorithm, according to the presented example, carries out a process that begins with processor 28 receiving EA data of endocardium and epicardium surfaces of a same region of a cardiac chamber, such as of left atrium 40, at EA data receiving step 70. In an example, the processor receives via interface circuits 35 EA mapping data acquired by catheter 29, as shown in FIG. 1. In another example, the processor uploads the EA data from memory 33 of system 21.

Next, at EA maps generation step 72, processor 28 generates separate endocardium and epicardium EA maps from the EA data. In alternative embodiment, the processor receives first and second surfaces that are, respectively, separate endocardium and epicardium EA maps.

Next, processor 28 derives an exploded EA map that shows both endocardium and epicardium EA map portions, at an exploded EA map derivation step 74. The processor may generate the exploded map by the method described in FIG. 2, e.g., providing views 202, or by other methods, such as using an exploded view.

At a map presentation step 76, processor 28 presents the exploded map on a display to a user, such as in views 202.

In an overlay generation step 78, processor 28 puts a draggable overlay 210 on the exploded EA map, to display on a window 204 side-by-side view of clipped views (216, 218) of a same region of the endocardium and epicardium EA maps.

Finally, at step 80, in response to a user moving marker 225, processor 28 drags side-by-side window 204 on view 202 to allow the user to zoom in on different regions of view 202, as shown in window 204.

The example flow chart shown in FIG. 3 is chosen purely for the sake of conceptual clarity. In optional examples, various additional steps may be performed, for example to automatically register additional layers, such as of medical images, and to generate and display respective overlay regions of the additional layers.

Example 1

A method includes receiving a first representation of an internal surface of at least a portion of a wall of an organ of a patient, and a second representation of an external surface of at least the portion of the wall of the organ. The first and second representations are registered with one another. An exploded representation (202) is generated from the first and second representations, that shows both the internal surface and the external surface. The exploded representation is presented to a user.

Example 2

The method according to example 1, wherein generating the exploded representation (202) comprises generating first and second clipped views (216, 218) of the respective first and second representations, and displacing the first and second clipped views from one another along a predefined direction.

Example 3

The method according to example 1 or example 2, wherein displacing the first and second clipped views (216, 218) from one another comprises causing the first and second clipped views to not overlap one another.

Example 4

The method according to any one of examples 1 through 3, wherein the internal surface is an endocardium and the external surface is an epicardium.

Example 5

The method according to any one of examples 1 through 4, wherein the first and second representations are electro-anatomical (EA) maps.

Example 6

The method according to any one of examples 1 through 5, wherein the EA maps comprise color coded EA maps.

Example 7

The method according to any one of examples 1 through 5, wherein the EA maps are local activation time (LAT) maps.

Example 8

The method according to example 1, wherein presenting the exploded representation (202) comprises generating a draggable overlay (210), and using the draggable overlay to display a side-by-side view of a corresponding region of the internal surface and the external surface.

Example 9

The method according to example 1, wherein the overlay (210) has a circular shape.

Example 10

The method according to example 1, and comprising selecting the region in response to positioning of the draggable overlay (210) by a user.

Example 11

A system (21) including a memory (33) and a processor (28). The memory is configured to store representations of surfaces of a wall of an organ of a patient. The processor is configured to (i) receive a first representation of an internal surface of at least a portion of the wall of the organ of the patient, and a second representation of an external surface of at least the portion of the wall of the organ, (ii) register the first and second representations with one another, (iii) generate from the first and second representations an exploded representation (202) that shows both the internal surface and the external surface, and (iv) present the exploded representation to a user.

Example 12

The system (21) according to example 11, wherein the processor is configured to generate the exploded representation (202) by generating first and second clipped views (216, 218) of the respective first and second representations, and displacing the first and second clipped views (216, 218) from one another along a predefined direction.

Example 13

The system (21) according to example 11 or example 12, wherein the processor (28) is configured to displace the first and second clipped views (216, 218) from one another by causing the first and second clipped views to not overlap one another.

Example 14

The system (21) according to any one of examples 1 through 13, wherein the internal surface is an endocardium and the external surface is an epicardium.

Example 15

The system (21) according to any one of examples 1 through 14, wherein the first and second representations are electroanatomical (EA) maps.

Example 16

The system (21) according to any one of examples 1 through 15, wherein the EA maps comprise color coded EA maps.

Example 17

The system (21) according to any one of examples 1 through 15, wherein the EA maps are local activation time (LAT) maps.

Example 18

The system (21) according to example 11, wherein the processor (28) is configured to present the exploded representation (202) by generating a draggable overlay (210), and using the draggable overlay to display a side-by-side view of a corresponding region of the internal surface and the external surface.

Example 19

The system (21) according to example 11, wherein the overlay (210) has a circular shape.

Example 20

The system (21) according to claim 11, wherein the processor (28) is further configured to selecting the region in response to positioning of the draggable overlay (210) by a user.

Although the examples described herein mainly address cardiac applications, the methods and systems described herein can also be used in other applications, such as in electroanatomical mapping of a brain.

It will thus be appreciated that the examples described above are cited by way of example, and that the present disclosure is not limited to what has been particularly shown and described hereinabove. Rather, the scope of the present disclosure includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method comprising:
generating a first three-dimensional (3D) electro-anatomical (EA) map of an endocardium surface and a second 3D EA map of an epicardium surface based on EA data collected from a patient's heart;
registering the first EA map to the second EA map;
rendering a 3D model including both the first EA and the second EA on a display;
tracking a user controlled draggable window displayed over the rendered 3D model, wherein the draggable window is configured to define a portion of the rendered display of the 3D model;
identifying the portion defined in each of the first EA map and the second EA map; and
rendering a first two-dimensional view of the portion defined in the first EA map alongside rendering a second two-dimensional view of the portion defined in the second EA map.

2. The method of claim 1, wherein the user controlled draggable window displayed is configured to define the portion of one of the first EA and the second EA and wherein the corresponding portion on the other of one of the first EA and the second EA is identified based on the registering.

3. The method of claim 1, wherein a size of the user controlled draggable window is configured to be adjustable based on user input.

4. The method of claim 1, further comprising updating the first and second two-dimensional views based on tracking movement of the user controlled draggable window.

5. The method of claim 1, wherein the 3D model including both the first EA and the second EA on a display is rendered on the display as an exploded view of the first EA map and the second EA map.

6. The method of claim 1, wherein the 3D model, user controlled draggable window, the first two-dimensional view and the second two-dimensional view are displayed simultaneously.

7. The method of claim 1, wherein each of the first EA map and the second EA map are configured to map local activation time (LAT).

8. A system, comprising:
a display;
a controller configured to receive electro-anatomical (EA) data of a patient's heart;
a processor configured to:
generate a first three-dimensional (3D) EA map of an endocardium surface of a patient's heart and a second 3D EA map of an epicardium surface of the patient's heart based on the EA data;
register the first EA map to the second EA map;
render a 3D model including both the first EA and the second EA on the display;
track a user controlled draggable window displayed over the rendered 3D model, wherein the draggable window is configured to define a portion of the rendered display of the 3D model;
identify the portion defined in each of the first EA map and the second EA map; and
render a first two-dimensional view of the portion defined in the first EA map alongside a rendered second two-dimensional view of the portion defined in the second EA map.

9. The system of claim 8, wherein the user controlled draggable window displayed is configured to define the portion of one of the first EA and the second EA and wherein the corresponding portion on the other of one of the first EA and the second EA is identified based on the registering.

10. The system of claim 8, wherein the processor is configured to adjust a size of the user controlled draggable window based on user input.

11. The system of claim 8, wherein the processor is configured to update the first and second two-dimensional views based on tracking movement of the user controlled draggable window.

12. The system of claim 8, wherein the 3D model including both the first EA and the second EA on a display is rendered on the display as an exploded view of the first EA map and the second EA map.

13. The system of claim 8, wherein the 3D model, user controlled draggable window, the first two-dimensional view and the second two-dimensional view are displayed simultaneously.

14. The system of claim 8, wherein each of the first EA map and the second EA map are configured to map local activation time (LAT).

* * * * *